(12) United States Patent
Banavara et al.

(10) Patent No.: US 10,639,334 B2
(45) Date of Patent: May 5, 2020

(54) PEDIATRIC NUTRITIONAL COMPOSITION WITH MILK PEPTIDES FOR HEALTHY GROWTH AND DEVELOPMENT

(71) Applicant: Mead Johnson Nutrition Company, Glenview, IL (US)

(72) Inventors: Dattatreya Banavara, Newburgh, IN (US); Roseanne P. Batema, Evansville, IN (US)

(73) Assignee: MEAD JOHNSON NUTRITION COMPANY, Evansville, IN (US)

( * ) Notice: Subject to any disclaimer, the term of this patent is extended or adjusted under 35 U.S.C. 154(b) by 0 days.

(21) Appl. No.: 14/149,424

(22) Filed: Jan. 7, 2014

(65) Prior Publication Data

US 2015/0189905 A1 Jul. 9, 2015

(51) Int. Cl.
| | | |
|---|---|---|
| *A61K 35/20* | (2006.01) | |
| *A61K 45/06* | (2006.01) | |
| *A61K 38/01* | (2006.01) | |
| *A61K 31/202* | (2006.01) | |
| *A23L 33/21* | (2016.01) | |
| *A23L 33/00* | (2016.01) | |
| *A23L 33/19* | (2016.01) | |
| *A23L 33/18* | (2016.01) | |
| *A23L 33/12* | (2016.01) | |
| *A23L 33/135* | (2016.01) | |
| *A23L 33/13* | (2016.01) | |
| *A23L 33/145* | (2016.01) | |

(52) U.S. Cl.
CPC .............. *A61K 35/20* (2013.01); *A23L 33/12* (2016.08); *A23L 33/13* (2016.08); *A23L 33/135* (2016.08); *A23L 33/145* (2016.08); *A23L 33/18* (2016.08); *A23L 33/19* (2016.08); *A23L 33/21* (2016.08); *A23L 33/40* (2016.08); *A61K 31/202* (2013.01); *A61K 38/018* (2013.01); *A61K 45/06* (2013.01); *A23V 2250/54242* (2013.01)

(58) Field of Classification Search
None
See application file for complete search history.

(56) References Cited

U.S. PATENT DOCUMENTS

| | | | |
|---|---|---|---|
| 4,791,193 A | 12/1988 | Okonogi et al. | |
| 5,374,567 A | 12/1994 | Cartagena | |
| 5,397,591 A | 3/1995 | Kyle | |
| 5,550,156 A | 8/1996 | Kyle | |
| 5,849,885 A | 12/1998 | Nuyens | |
| 5,861,491 A | 1/1999 | Nuijens | |
| 5,919,913 A | 7/1999 | Nuyens | |
| 7,368,141 B2 | 5/2008 | Lihme | |
| 2006/0286252 A1* | 12/2006 | Rangavajla et al. | 426/580 |
| 2009/0075904 A1* | 3/2009 | Boots | A61K 38/018 514/1.1 |
| 2009/0162521 A1 | 6/2009 | Clinger et al. | |

FOREIGN PATENT DOCUMENTS

WO 2013055438 4/2013

OTHER PUBLICATIONS

Dupont (Protein requirements during the first year of life; Am J Clin Nutr ;2003; 77).*
Casein from bovine milk (Sigma product information, accessed Jan. 7, 2015).*
Kontopidis et al. (J. Dairy Sci. Apr. 2004; 87(4): 785-96).*
Atkinson, S., et al., "The Non-Protein Nitrogen Components in Human Milk: Biochemistry and Potential Functional Role," CRC Press, Inc. 1989, pp. 117-133.
Febba, A., et al., "Stunting growth: association of the blood pressure levels and ACE activity in early childhood," Pediatr Nephrol (2009) 24:379-386. (Abstract Only).
Greenberg, R., et al., "Human B-Casein Amino Acid Sequence and Identification of Phosphorylation Sites," vol. 259, No. 8, Issue of Apr. 25, pp. 5132-5138, 1984.
Hartmann, R., et al., "Food-derived peptides with biological activity: from research to food applications," Current Opinion in Biotechnology 2007, 18:163-169.
Jefferies-Grant, K., "Comparative Analysis of Human Milk Peptides: Gestational and Lactation Stage Effects," Dissertation submitted to the Department of Chemistry & Biochemistry, Florida State University, 2008.
Yadomae, T., Structure and biological activities of fungal beta-1,3-glucans. Yakugaku Zasshi. 2000;120:413-431.
Database WPI Week 201129, Mar. 23, 2011 Thomson Scientific, London, GB; AN 2011-E23756 XP002736875, "Nutritious milk powder, useful for reducing protein allergy in infants, comprises fresh milk, desalted whey powder, refined vegetable oil, lactose, whey peptides, fructooligosaccharides arachidonic acid, dihyroxyacetone and nucleotides".

* cited by examiner

*Primary Examiner* — James H Alstrum-Acevedo
*Assistant Examiner* — Tara L Martinez
(74) *Attorney, Agent, or Firm* — Troutman Sanders LLP; Ryan Schneider; Chris Davis

(57) ABSTRACT

The present disclosure generally provides pediatric nutritional compositions comprising a protein source comprising an intact milk protein and a partially hydrolyzed milk protein, wherein about 5% to about 25% of total nitrogen content of the composition is non-protein nitrogen. The pediatric nutritional compositions described herein also comprise a fat source and a carbohydrate source. The partially hydrolyzed protein source, in certain embodiments, provides peptides that have similar structure and function to the peptides found in human milk.

16 Claims, No Drawings
Specification includes a Sequence Listing.

PEDIATRIC NUTRITIONAL COMPOSITION WITH MILK PEPTIDES FOR HEALTHY GROWTH AND DEVELOPMENT

TECHNICAL FIELD

The present disclosure generally relates pediatric nutritional compositions, such as infant formulas and other children's nutritional products, comprising a protein source having an intact milk protein and partially hydrolyzed milk protein. More specifically, about 5% to about 25% of the total nitrogen content of the composition is provided by the partially hydrolyzed milk protein. The partially hydrolyzed milk protein may be derived from whey, casein or a combination thereof.

BACKGROUND

Pediatric nutritional products, particularly infant formulas, are designed to mimic human milk as closely as possible. Human milk contains numerous macro and micronutrient components, the identity and function of which are still being discovered and studied. One essential macronutrient important for growth and development is protein. Human milk contains both intact proteins and peptides, and has a unique peptide profile that contributes to many of the health benefits of human milk. Some of the peptides in human milk (molecular weight of less than 12 kDa, and more particularly, less than 5 kDa) have been identified as fragments of human milk β-casein and other proteins, such as IGF-1, TGF-β, and ghrelin. Certain human milk peptides derived from human milk β-casein have been sequenced and their properties identified, including isoelectric point (pI), solubility and charge at neutral pH determine the cationic/anionic nature of a particular peptide.

In addition to having a unique peptide profile, the nitrogen distribution of human milk is unique. Approximately 75% to 80% of total nitrogen content of human milk is provided by intact proteins, and approximately 20% to 25% of total nitrogen is provided by non-protein nitrogen. Non-protein nitrogen in human milk includes peptides, free amino acids, polyamines, nucleotides, urea, and sialic acid. More specifically, approximately 10% to 15% of total nitrogen in human milk is provided by the non-protein nitrogen small peptides and free amino acids. Human milk peptides also provide important functional benefits, including antioxidant, antimicrobial, antiviral, angiotension converting enzyme (ACE) inhibitory and immunomodulatory activities. Furthermore, human milk peptides are believed to contribute additional benefits to human milk, such as improving sleep and reducing stress in infants.

Routine pediatric milk based nutritional compositions, such as those not intended for allergic individuals, generally include intact protein sources such as whey, casein or mixtures of both. Caseins of bovine milk include αS1, αS2, κ and β-casein. Bovine milk contains similar amounts of β-casein as human milk and has a sequence homology to human β-casein of about 50%. Bovine whey includes several major milk proteins such as β-lactoglobulin, α-lactalbumin, bovine serum albumin, and immunoglobulins.

Nevertheless, such routine nutritional compositions based on intact casein and/or whey do not have a peptide or nitrogen distribution profile similar to that of human milk, nor do they provide as many beneficial functions that are found in human milk. Accordingly, it would be advantageous to provide a pediatric nutritional composition that more closely mimics the nitrogen distribution profile of human milk. Furthermore, it would be desirable to provide a pediatric nutritional composition that closely mimics the peptide profile of human milk by including functional peptides that are similar in structure and/or function to the peptides found in human milk, such as peptides having antioxidant, antimicrobial, antiviral, ACE inhibitory and immunomodulatory activities. The present disclosure addresses these needs.

BRIEF SUMMARY

The present disclosure relates generally to pediatric nutritional compositions having a nitrogen distribution and/or peptide profile similar to that of human milk. Briefly, the present disclosure relates to a pediatric nutritional composition in which about 5% to about 25% of the nitrogen content of the composition is non-protein nitrogen. More particularly, the present disclosure is directed to, in certain embodiments, a nutritional composition comprising a protein source comprising an intact milk protein and a partially hydrolyzed milk protein, wherein about 5% to about 25% of total nitrogen content of the composition is non-protein nitrogen. The partially hydrolyzed milk protein, in certain embodiments, comprises partially hydrolyzed whey, casein, or a mixture thereof. The nutritional composition also includes a fat source and a carbohydrate source.

In particular embodiments, the partially hydrolyzed milk protein comprises at least one peptide containing a sequence selected from the group consisting of SEQ ID Nos. 1 to 9. In other embodiments, the partially hydrolyzed milk protein comprises at least one peptide selected from the group consisting of SEQ ID Nos. 10-53.

While not being bound by any particularly theory, it is believed that the present compositions advantageously provide a nitrogen distribution profile similar to that found in human milk. Additionally, the peptides provided by the hydrolyzed milk protein also may have similar chemistry and/or functionality as the peptides found in human milk. For example, the peptides of the present compositions may have beneficial functional properties, such as antioxidant, antimicrobial, antiviral, ACE inhibitory, and immunomodulatory properties.

The pediatric nutritional compositions provided herein are, in some embodiments, nutritionally complete, and are designed for infants. In other embodiments, the pediatric nutritional compositions are designed for older pediatric subjects, such as children having an age from about one to about six years, or about 1 to about 3 years. Such nutritional products may or may not be nutritionally complete, and include compositions such as growing up milks.

The nutritional compositions described herein may include, in certain embodiments, additional ingredients, such as polyunsaturated fatty acids, prebiotics, probiotics, beta-glucan, nucleotides, vitamins and minerals, and/or lactoferrin.

The present disclosure also provides methods for providing nutrition to a pediatric subject, comprising administering to a pediatric subject any of nutritional compositions described herein.

It is to be understood that both the foregoing general description and the following detailed description present embodiments of the disclosure and are intended to provide an overview or framework for understanding the nature and character of the disclosure as it is claimed. The description serves to explain the principles and operations of the claimed subject matter. Other and further features and advantages of the present disclosure will be readily apparent to those skilled in the art upon a reading of the following disclosure.

DETAILED DESCRIPTION

Reference now will be made in detail to the embodiments of the present disclosure, one or more examples of which are set forth herein below. Each example is provided by way of explanation of the nutritional composition of the present disclosure and is not a limitation. In fact, it will be apparent to those skilled in the art that various modifications and variations can be made to the teachings of the present disclosure without departing from the scope or spirit of the disclosure. For instance, features illustrated or described as part of one embodiment, can be used with another embodiment to yield a still further embodiment.

Thus, it is intended that the present disclosure covers such modifications and variations as come within the scope of the appended claims and their equivalents. Other objects, features and aspects of the present disclosure are disclosed in or are obvious from the following detailed description. It is to be understood by one of ordinary skill in the art that the present discussion is a description of exemplary embodiments only and is not intended as limiting the broader aspects of the present disclosure.

"Nutritional composition" means a substance or formulation that satisfies at least a portion of a subject's nutrient requirements. The terms "nutritional(s)," "nutritional formula(s)," "enteral nutritional(s)," "nutritional composition(s)," and "nutritional supplement(s)" are used interchangeably throughout the present disclosure to refer to liquids, powders, gels, pastes, solids, concentrates, suspensions, or ready-to-use forms of enteral formulas, oral formulas, formulas for infants, formulas for pediatric subjects, formulas for children, growing-up milks and/or formulas for adults, such as women who are lactating or pregnant. In particular embodiments, the nutritional compositions are for pediatric subjects, including infants and children.

The term "enteral" means through or within the gastrointestinal, or digestive, tract. "Enteral administration" includes oral feeding, intragastric feeding, transpyloric administration, or any other administration into the digestive tract.

"Pediatric subject" includes both infants and children, and refers herein to a human that is less than thirteen years of age. In some embodiments, a pediatric subject refers to a human subject that is less than eight years old. In other embodiments, a pediatric subject refers to a human subject between about one and about six years of age or about one and about three years of age. In still further embodiments, a pediatric subject refers to a human subject between about 6 and about 12 years of age.

"Infant" means a subject having an age of not more than about one year and includes infants from about zero to about twelve months. The term infant includes low birth weight infants, very low birth weight infants, and preterm infants. "Preterm" means an infant born before the end of the 37th week of gestation, while "full term" means an infant born after the end of the 37th week of gestation.

"Child" means a subject ranging in age from about twelve months to about thirteen years. In some embodiments, a child is a subject between the ages of one and twelve years old. In other embodiments, the terms "children" or "child" refer to subjects that are between about one and about six years old, between about one and about three years old, or between about seven and about twelve years old. In other embodiments, the terms "children" or "child" refer to any range of ages between about 12 months and about 13 years.

"Children's nutritional product" refers to a composition that satisfies at least a portion of the nutrient requirements of a child. A growing-up milk is an example of a children's nutritional product.

"Infant formula" means a composition that satisfies at least a portion of the nutrient requirements of an infant. In the United States, the content of an infant formula is dictated by the federal regulations set forth at 21 C.F.R. Sections 100, 106, and 107. These regulations define macronutrient, vitamin, mineral, and other ingredient levels in an effort to simulate the nutritional and other properties of human breast milk.

The term "growing-up milk" refers to a broad category of nutritional compositions intended to be used as a part of a diverse diet in order to support the normal growth and development of a child between the ages of about 1 and about 6 years of age.

"Milk-based" means comprising at least one component that has been drawn or extracted from the mammary gland of a mammal. In some embodiments, a milk-based nutritional composition comprises components of milk that are derived from domesticated ungulates, ruminants or other mammals or any combination thereof. Moreover, in some embodiments, milk-based means comprising bovine casein, whey, lactose, or any combination thereof. Further, "milk-based nutritional composition" may refer to any composition comprising any milk-derived or milk-based product known in the art.

"Nutritionally complete" means a composition that may be used as the sole source of nutrition, which would supply essentially all of the required daily amounts of vitamins, minerals, and/or trace elements in combination with proteins, carbohydrates, and lipids. Indeed, "nutritionally complete" describes a nutritional composition that provides adequate amounts of carbohydrates, lipids, essential fatty acids, proteins, essential amino acids, conditionally essential amino acids, vitamins, minerals and energy required to support normal growth and development of a subject.

Therefore, a nutritional composition that is "nutritionally complete" for a preterm infant will, by definition, provide qualitatively and quantitatively adequate amounts of carbohydrates, lipids, essential fatty acids, proteins, essential amino acids, conditionally essential amino acids, vitamins, minerals, and energy required for growth of the preterm infant.

A nutritional composition that is "nutritionally complete" for a term infant will, by definition, provide qualitatively and quantitatively adequate amounts of all carbohydrates, lipids, essential fatty acids, proteins, essential amino acids, conditionally essential amino acids, vitamins, minerals, and energy required for growth of the term infant.

A nutritional composition that is "nutritionally complete" for a child will, by definition, provide qualitatively and quantitatively adequate amounts of all carbohydrates, lipids, essential fatty acids, proteins, essential amino acids, conditionally essential amino acids, vitamins, minerals, and energy required for growth of a child.

As applied to nutrients, the term "essential" refers to any nutrient that cannot be synthesized by the body in amounts sufficient for normal growth and to maintain health and that, therefore, must be supplied by the diet. The term "conditionally essential" as applied to nutrients means that the nutrient must be supplied by the diet under conditions when adequate amounts of the precursor compound is unavailable to the body for endogenous synthesis to occur.

"Nutritional supplement" or "supplement" refers to a formulation that contains a nutritionally relevant amount of at least one nutrient. For example, supplements described herein may provide at least one nutrient for a human subject, such as a lactating or pregnant female.

"Probiotic" means a microorganism with low or no pathogenicity that exerts a beneficial effect on the health of the host.

The term "inactivated probiotic" means a probiotic wherein the metabolic activity or reproductive ability of the probiotic organism has been reduced or destroyed. An "inactivated probiotic" does, nevertheless, still retain at the cellular level at least a portion of its biological glycolprotein and DNA/RNA structure. As used herein, the term "inactivated" is synonymous with "non-viable." A non-limiting example of an inactivated probiotic is inactivated *Lactobacillus rhamnosus* GG ("LGG").

"Prebiotic" means a non-digestible food ingredient that beneficially affects the host by selectively stimulating the growth and/or activity of one or a limited number of beneficial gut bacteria in the digestive tract, selective reduction in gut pathogens, or favorable influence on gut short chain fatty acid profile that can improve the health of the host.

"β-glucan" means all β-glucan, including both β-1,3-glucan and β-1,3; 1,6-glucan, as each is a specific type of β-glucan. Moreover, β-1,3; 1,6-glucan is a type of β-1,3-glucan. Therefore, the term "β-1,3-glucan" includes β-1,3; 1,6-glucan.

All percentages, parts and ratios as used herein are by weight of the total formulation, unless otherwise specified.

The nutritional composition of the present disclosure may be free of substantially free of any optional or selected ingredients described herein. In this context, and unless otherwise specified, the term "substantially free" means that the selected composition may contain less than a functional amount of the optional ingredient, typically less than 0.1% by weight, and also, including zero percent by weight of such optional or selected ingredient.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The compositions and methods of the present disclosure, including components thereof, can comprise, consist of, or consist essentially of the essential elements and limitations of the embodiments described herein, as well as any additional or optional ingredients, components or limitations described herein or otherwise useful in nutritional compositions.

As used herein, the term "about" should be construed to refer to both of the numbers specified in any range. Any reference to a range should be considered as providing support for any subset within that range.

The present disclosure relates generally to pediatric nutritional compositions comprising an intact protein and a partially hydrolyzed milk protein, wherein in about 5% to about 25% of the total nitrogen content of the composition is non-protein nitrogen. The present compositions have an advantageous nitrogen distribution profile that is similar to the nitrogen distribution profile of human milk. In further embodiments, about 75% to about 95% of the nitrogen content of the composition is provided by the intact protein. The compositions also include a fat source and carbohydrate source.

Non-protein nitrogen sources in the present compositions include the partially hydrolyzed milk protein, which contains peptides and, in some embodiments, amino acids. In some embodiments, about 5% to about 25% of the total nitrogen content of the composition is peptides and provided by the partially hydrolyzed milk protein. In other embodiments, about 5% to about 20%, or about 10% to about 15% of the total nitrogen content of the composition is peptides and provided by the partially hydrolyzed milk protein. Additional source of non-protein nitrogen that are present in some embodiments include nucleotides, carnitine, lecithin, and mixtures thereof. In some embodiments, about less than 5% of the non-protein nitrogen in the composition comprises nucleotides, carnitine, lecithin, and mixtures thereof.

The partially hydrolyzed milk protein, in certain embodiments, comprises whey, casein, or a mixture thereof. In particular embodiments, the partially hydrolyzed milk protein comprises whey and casein in a ratio similar to the ratio of whey and casein found in human milk. More specifically, the partially hydrolyzed milk protein comprises, in certain embodiments, whey and casein having a whey to casein weight ratio ranging from about 80:20 to 20:80, about 80:20 to about 40:60, about 80:20 to about 50:50, or about 80:20 to about 60:40. In other embodiments, the partially hydrolyzed milk protein is a casein protein hydrolysate, while in still further embodiments, the partially hydrolyzed milk protein is a whey protein hydrolysate.

In some embodiments, about 75% to about 95% of the total nitrogen content of the composition is provided by the intact milk protein. The intact milk protein may be selected from whey, casein, and mixtures thereof. In some embodiments, the intact protein is a mixture of whey and casein, such as a mixture of whey and casein having a whey to casein ration of 80:20 to 50:50.

Furthermore, the present composition comprises about 1.4 g to about 3.8 g of total protein per 100 kcal of the composition. In more particular embodiments, the composition comprises about 1.8 to about 3.5 g of total protein per 100 kcal of the composition. In still further embodiments, the composition comprises about 2.1 g of total protein per 100 kcal of the composition. The total protein content of the composition includes both the intact milk protein and the partially hydrolyzed milk protein, and in some embodiments may also include amino acids. In certain embodiments, about 5 to about 25% of the protein source is the partially hydrolyzed milk protein, and in other embodiments, about 10 to about 15% of the total protein is the partially hydrolyzed milk protein.

The partially hydrolyzed milk protein has, in some embodiments, a degree of hydrolysis ranging from about 4% to about 40%, and more particularly, ranging from about 6% to about 12%. In certain embodiments, the partially hydrolyzed milk protein comprises peptides having sequences that match or are similar to the sequences of human milk peptides. Additionally, the partially hydrolyzed milk protein contains, in some embodiments, functional peptides having antioxidant, antimicrobial, antiviral, immunomodulatory and/or ACE inhibitory activity. ACE inhibitory peptides present in the composition may alleviate the stunted growth found in children with a high level of ACE activity.

The partially hydrolyzed milk protein used in the present composition comprises peptides having, in certain embodiments, molecular weights below about 12 kDa, more particularly, less than about 10 kDa, and even more particularly, less than about 5 kDa. In particular embodiments, at least 75% of the peptides have a molecular weight of less than 5 kDa, and in more particular embodiments, at least 80%, at least 85%, at least 90% or at least 95% of the peptides have a molecular weight of less than 5 kDa. More specifically, the peptides useful in the present compositions have a molecular weight ranging from about 0.3 kDa to about 12 KDa, about 0.3 to about 10 KDa, or about 0.5 to about 5 kDa.

The partially hydrolyzed milk protein comprises, in certain embodiments, peptides derived from casein and whey. More specifically, the partially hydrolyzed milk protein comprises, in certain embodiments, of β-casein, α-S1-casein, κ-casein, α-lactalbumin, β-lactoglobulin, interleukin-2 (IL-2), transforming growth factor-β (TGF-β), insulin-like growth factor-1 (IGF-1), glycosylation-dependent cell adhesion molecule-1 (GLYCAM-1), serum deprivation-response protein (SDPR) protein, and combinations thereof.

The peptides, in certain embodiments, include certain partial peptide sequences. For example, in certain embodiments, the partially hydrolyzed milk protein comprises at least one core peptide sequence selected from the group consisting of SEQ ID No. 1, SEQ ID No. 2, SEQ ID No. 3, SEQ ID No. 4, SEQ ID No. 5, SEQ ID No. 6, SEQ ID No. 7, SEQ ID No. 8, and SEQ ID No. 9. SEQ ID Nos. 1-9 are listed in Table 1, below.

TABLE 1

Core peptide sequences of partially hydrolyzed milk protein

| SEQ ID | Parent Protein | Peptide Sequence |
| --- | --- | --- |
| 1 | β-Casein | VPYPQ |
| 2 | β-Casein | LPVPQ |
| 3 | β-Lactoglobulin | DDEALEK |
| 4 | β-Lactoglobulin | VEELKP |
| 5 | β-Lactoglobulin | PEGDLE |
| 6 | α-S1-Casein | KEDVPSERY |
| 7 | GLYCAM-1 | NKPEDETH |
| 8 | β-Lactoglobulin | SAPLRVY |
| 9 | Uncharacterized | EVPK |

Some of these sequences are identical to or similar to sequences found in human milk peptides. Furthermore, while not being bound by theory, it is believed that these sequences may provide advantageous functional properties to the peptides containing them.

Exemplary peptides identified in partially hydrolyzed milk proteins useful for the present compositions are listed in Table 2, below. The peptide charge and proposed or reported peptide function is also provided in Table 2.

TABLE 2

Isolated peptide sequence, charge and proposed or reported functional properties

| SEQ ID | Parent Protein | Peptide Sequence | Charge | Function |
| --- | --- | --- | --- | --- |
| 10 | β-Casein | VPYPQRDMP | Neutral | |
| 11 | β-Casein | KVLPVPQK | Cationic | Antimicrobial/Immunomodulatory |
| 12 | β-Lactoglobulin | SDISLLDAQ | Anionic | Antioxidant |
| 13 | β-Lactoglobulin | DDEALEKFDKA | Anionic | Antioxidant |
| 14 | β-Lactoglobulin | LKPTPEGDLEILLQK | Anionic | Antioxidant |
| 15 | β-Lactoglobulin | LVRTPEVDDEALEKF | Anionic | Antioxidant |
| 16 | β-Lactoglobulin | TPEVDDEALEKF | Anionic | Antioxidant |
| 17 | β-Lactoglobulin | VDDEALEKF | Anionic | Antioxidant |
| 18 | β-Lactoglobulin | VEELKPTPEGDLE | Anionic | Antioxidant |
| 19 | β-Lactoglobulin | VEELKPTPEGDLEILLQK | Anionic | Antioxidant |
| 20 | β-Lactoglobulin/IL-2 | VEELKP | Anionic | Antioxidant |
| 21 | β-Lactoglobulin | VYVEELKPTPEGDLE | Anionic | Antioxidant |
| 22 | β-Lactoglobulin | DDEALEK | Anionic | Antioxidant |
| 23 | β-Lactoglobulin | LKPTPEGDLEILLQK | Anionic | Antioxidant |
| 24 | β-Lactoglobulin | RTPEVDDEALEK | Anionic | Antioxidant |
| 25 | α-S1-Casein | IGSENSEKT | Anionic | Antioxidant |
| 26 | α-S1-Casein | HIQKEDVPSERY | Anionic | Antioxidant |
| 27 | α-S1-Casein | KEDVPSERY | Anionic | Antioxidant |
| 28 | GLYCAM-1 | LNKPEDETH | Anionic | Antioxidant |
| 29 | GLYCAM-1 | NKPEDETHLEAQPT | Anionic | Antioxidant |
| 30 | κ-Casein | VIESPPEINT | Anionic | Antioxidant |
| 31 | Uncharacterized | WLVISVLAISLASSVTEDVC | Anionic | Antioxidant |
| 32 | Uncharacterized | NELTNSTLATDPP | Anionic | Antioxidant |
| 33 | Uncharacterized | QNAVPYPGGQGEAERFMTP | Anionic | Antioxidant |
| 34 | Uncharacterized | ITLHEALAAADDLSKQGISLRVI | Anionic | Antioxidant |
| 35 | β-Lactoglobulin | ASDISLLDAQSAPLRVY | Anionic | Antioxidant |
| 36 | β-Lactoglobulin | SAPLRVY | Cationic | Antimicrobial/Immunomodulatory/ACE inhibitory |
| 37 | β-Lactoglobulin | FDKALKALPM | Cationic | Antimicrobial/Immunomodulatory |
| 38 | β-Lactoglobulin | IIAEKTKIPA | Cationic | Antimicrobial/Immunomodulatory/Hypocholesterolemic |
| 39 | β-Lactoglobulin | KVLVLDTDYKKY | Cationic | Antimicrobial/Immunomodulatory |
| 40 | β-Lactoglobulin | LIVTQTMKGL | Cationic | Antimicrobial/Immunomodulatory |
| 41 | β-Lactoglobulin | LKP | Cationic | Antimicrobial/Immunomodulatory/ACE inhibitory |
| 42 | β-Casein | HKEMPFPKYP | Cationic | Antimicrobial/Immunomodulatory |

TABLE 2-continued

Isolated peptide sequence, charge and proposed or reported functional properties

| SEQ ID | Parent Protein | Peptide Sequence | Charge | Function |
|---|---|---|---|---|
| 43 | β-Casein | HQPHQPLPPT | Cationic | Antimicrobial/Immunomodulatory |
| 44 | β-Casein | SQSKVLPVPQK | Cationic | Antimicrobial/Immunomodulatory |
| 45 | GLYCAM-1 | SSRQPQSQNPKLP | Cationic | Antimicrobial/Immunomodulatory |
| 46 | κ-Casein | LSRYPSYG | Cationic | Antimicrobial/Immunomodulatory |
| 47 | α-Lactalbumin | KILDKVGINY | Cationic | Antimicrobial/Immunomodulatory |
| 48 | Uncharacterized | VVGRGPGTP | Cationic | Antimicrobial/Immunomodulatory |
| 49 | Uncharacterized | LKIQNLELKLSGDSRASRTKSTPSTCE | Cationic | Antimicrobial/Immunomodulatory |
| 50 | Uncharacterized | LASIMNPKSLTIGPRDKPT | Cationic | Antimicrobial/Immunomodulatory |
| 51 | Uncharacterized | YKETLNLKSQVQK | Cationic | Antimicrobial/Immunomodulatory |
| 52 | SDPR Protein | LKPEGEARHPLTTSPSHRGQRKVPI | Cationic | Antimicrobial/Immunomodulatory |
| 53 | Uncharacterized | EVPKPEVIFKLEQ | Neutral | Unknown |

Accordingly, in certain embodiments, the partially hydrolyzed milk protein comprises at least one peptide selected from SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, SEQ ID No. 39, SEQ ID No. 40, SEQ ID No. 41, SEQ ID No. 42, SEQ ID No. 43, SEQ ID No. 44, SEQ ID No. 45, SEQ ID No. 46, SEQ ID No. 47, SEQ ID No. 48, SEQ ID No. 49, SEQ ID No. 50, SEQ ID No. 51, SEQ ID No. 52, and SEQ ID 53. In some embodiments, the partially hydrolyzed milk protein contains several of the aforementioned peptides, such as at least 5, at least 10, at least 20, at least, at least 40, or even all of SEQ ID Nos. 10 to 53. More particularly, in some embodiments, the partially hydrolyzed milk protein comprises the peptide sequences in table 2 that are derived from β-casein. In other embodiments, the partially hydrolyzed milk protein comprises the peptide sequences in table 2 that are derived from β-lactoglobulin. In still other embodiments, the partially hydrolyzed milk protein comprises the peptide sequences in table 2 that are derived from α-S1-casein. In further embodiments, the partially hydrolyzed milk protein comprises the peptide sequences in table 2 that are derived from GLYCAM-1. In yet other embodiments, the partially hydrolyzed milk protein comprises the peptide sequences in table 2 that are derived from κ-casein. In still other embodiments, the partially hydrolyzed milk protein comprises the peptide sequences in table 2 that are derived from α-lactalbumin. Finally, in some embodiments, in some embodiments, the partially hydrolyzed milk protein comprises the peptide sequences in table 2 that are derived from any combination of β-casein, β-lactoglobulin, α-S1-casein, GLYCAM-1, κ-casein, and α-lactalbumin. Furthermore, in some embodiments, the composition described herein comprises about 1 mg to about 500 mg of one or more of SEQ ID Nos. 10-53 per 100 kcal of the composition.

The milk peptides described above are furthermore believed to provide at least 5 mM of Trolox equivalent antioxidant capacity to the nutritional compositions described herein. Trolox (6-hydroxy-2,5,7,8-tetramethylchroman-2-carboxylic acid) is a water-soluble analog of vitamin E sold by F. Hoffman-LaRoche, Ltd. It is an antioxidant like vitamin E and it is used in biological or biochemical applications to reduce oxidative stress or damage. Trolox equivalent antioxidant capacity is a measurement of antioxidant strength based on Trolox, measured in units called Trolox Equivalents (TE), e.g. micromole TE/100 g. Due to the difficulties in measuring individual antioxidant components of a complex mixture, Trolox equivalency is used as a benchmark for the antioxidant capacity of such a mixture. Trolox equivalency is most often measured using the 2,2'-azino-bis(3-ethylbenzothiazoline-6-sulphonic acid) (ABTS) decolorization assay. The Trolox equivalent antioxidant capacity assay is used in the art to measure antioxidant capacity of foods, beverages and supplements.

While not being bound by theory, the peptides in the hydrolyzed milk protein may, in certain embodiments, be functionally similar or equivalent to peptides found in human milk due to their peptide sequences, and therefore may impart similar antimicrobial, antibacterial, antiviral, ACE inhibitory and immunomodulatory activities. These peptides also may help infants sleep better and reduce infant stress. Furthermore, peptides that are rich in glutamic acid and glutamine are believed to play a role in the development of the brain and nervous system because glutamate acts a principal neurotransmitter in the brain.

Moreover, β-lactoglobulin is considered a major allergen in bovine milk. Thus, the reduction of intact β-lactoglobulin by using a protein source containing approximately 5 to 25% of partially hydrolyzed milk protein reduces the allergen content of the composition. Additionally, the presence of peptides of β-lactoglobulin may facilitate the development of milk protein tolerance later in a pediatric subject's life.

The present disclosure also provides methods for providing nutritional to a pediatric subject comprising administering to the subject any of the aforementioned nutritional compositions.

The disclosed nutritional composition(s) may be provided in any form known in the art, such as a powder, a gel, a suspension, a paste, a solid, a liquid, a liquid concentrate, a reconstitutable powdered milk substitute or a ready-to-use product. The nutritional composition may, in certain embodiments, comprise a nutritional supplement, children's nutritional product, infant formula, human milk fortifier, growing-up milk or any other nutritional composition designed for a pediatric subject. Nutritional compositions of the present disclosure include, for example, orally-ingestible, health-promoting substances including, for example, foods, beverages, tablets, capsules and powders. Moreover, the nutritional composition of the present disclosure may be standardized to a specific caloric content, it may be provided as a ready-to-use product, or it may be provided in a concentrated form. In some embodiments, the nutritional composition is in powder form with a particle size in the range of 5 µm to 1500 µm, more preferably in the range of 10 µm to 1000 µm, and even more preferably in the range of 50 µm to 300 µm.

In some embodiments, the nutritional composition is an infant formula suitable for infants ranging in age from 0 to 12 months, from 0 to 3 months, 0 to 6 months or 6 to 12 months. In other embodiments, the disclosure provides a fortified milk-based growing-up milk designed for children ages 1-3 years and/or 4-6 years, wherein the growing-up milk supports growth and development and life-long health.

The protein source of the present nutritional compositions may comprise, in addition to the partially hydrolyzed milk protein, other protein sources, particularly intact protein sources commonly used in the art, e.g., nonfat milk, whey protein, casein, soy protein, whole protein, hydrolyzed protein, and the like. Bovine milk protein sources useful in practicing the present disclosure include, but are not limited to, milk protein powders, milk protein concentrates, milk protein isolates, nonfat milk solids, nonfat milk, nonfat dry milk, whey protein, whey protein isolates, whey protein concentrates, sweet whey, acid whey, casein, acid casein, caseinate (e.g. sodium caseinate, sodium calcium caseinate, calcium caseinate) and any combinations thereof. In yet another embodiment, the protein source may be supplemented with glutamine-containing peptides. In a particular embodiment, the intact protein source comprises casein protein, whey protein, or a combination thereof.

The amount of protein in the nutritional composition comprises, in certain embodiments, between about 1 g and about 5 g of protein per 100 kcal. In other embodiments, the amount of protein comprises between about 1.4 and about 3.5 g per 100 kcal.

Suitable fat or lipid sources for the nutritional composition of the present disclosure may be any known or used in the art, including but not limited to, animal sources, e.g., milk fat, butter, butter fat, egg yolk lipid; marine sources, such as fish oils, marine oils, single cell oils; vegetable and plant oils, such as corn oil, canola oil, sunflower oil, soybean oil, palm olein oil, coconut oil, high oleic sunflower oil, evening primrose oil, rapeseed oil, olive oil, flaxseed (linseed) oil, cottonseed oil, high oleic safflower oil, palm stearin, palm kernel oil, wheat germ oil; medium chain triglyceride oils and emulsions and esters of fatty acids; and any combinations thereof.

Carbohydrate sources can be any used in the art, e.g., lactose, glucose, fructose, corn syrup solids, maltodextrins, sucrose, starch, rice syrup solids, and the like. The amount of carbohydrate in the nutritional composition typically can vary from between about 5 g and about 25 g/100 kcal.

In one embodiment, the nutritional composition may contain one or more probiotics. Any probiotic known in the art may be acceptable in this embodiment. In a particular embodiment, the probiotic may be selected from any *Lactobacillus* species, *Lactobacillus rhamnosus* GG (e.g., ATCC number 53103), *Bifidobacterium* species, *Bifidobacterium longum* (e.g. AH1205 or AH1206), and *Bifidobacterium animalis* subsp. *lactis* BB-12 (DSM No. 10140), *Bifidobacterium infantis* (e.g. 35624), or any combination thereof.

If included in the composition, the amount of the probiotic may vary from about $1 \times 10^4$ to about $1 \times 10^{12}$ colony forming units (cfu) per gram of the nutritional composition. In another embodiment, the amount of the probiotic may vary from about $1 \times 10^6$ to about $1 \times 10^{12}$ cfu per gram of the nutritional composition. In still another embodiment, the amount of the probiotic may vary from about $1 \times 10^6$ to about $1 \times 10^9$ cfu per gram of the nutritional composition, or about $1 \times 10^9$ to about $1 \times 10^{12}$ cfu per gram of the nutritional composition. In yet another embodiment, the amount of the probiotic may be at least about $1 \times 106$ cfu per gram of the nutritional composition.

In an embodiment, the probiotic(s) may be viable or non-viable. As used herein, the term "viable", refers to live microorganisms. The term "non-viable" or "non-viable probiotic" means non-living probiotic microorganisms, their cellular components and/or metabolites thereof. Such non-viable probiotics may have been heat-killed or otherwise inactivated, but they retain the ability to favorably influence the health of the host. The probiotics useful in the present disclosure may be naturally-occurring, synthetic or developed through the genetic manipulation of organisms, whether such new source is now known or later developed.

The nutritional composition may also contain one or more prebiotics in certain embodiments. Such prebiotics may be naturally-occurring, synthetic, or developed through the genetic manipulation of organisms and/or plants, whether such new source is now known or developed later. Prebiotics useful in the present disclosure may include oligosaccharides, polysaccharides, and other prebiotics that contain fructose, xylose, soya, galactose, glucose and mannose.

More specifically, prebiotics useful in the present disclosure may include polydextrose, polydextrose powder, lactulose, lactosucrose, raffinose, gluco-oligosaccharide, inulin, fructo-oligosaccharide, isomalto-oligosaccharide, soybean oligosaccharides, lactosucrose, xylo-oligosaccharide, chito-oligosaccharide, manno-oligosaccharide, aribino-oligosaccharide, siallyl-oligosaccharide, fuco-oligosaccharide, galacto-oligosaccharide, and gentio-oligosaccharides.

In an embodiment, the total amount of prebiotics present in the nutritional composition may be from about 1.0 g/L to about 10.0 g/L of the composition. For example, in some embodiments, polydextrose (PDX) may be included in the nutritional composition in an about of about 1.0 to 10 g/L. In another embodiment, the amount of PDX is about 2.0 to about 8.0 g/L.

In certain embodiments, at least 20% of the prebiotics can comprise galacto-oligosaccharide (GOS), (PDX) or a mixture thereof. In an embodiment, the PDX and GOS have a PDX:GOS ratio of between about 9:1 and 1:9. In another embodiment, the ratio of PDX:GOS can be about 5:1 to 1:5. In yet another embodiment, the ratio of PDX:GOS can be between about 1:3 and 1:3. In further more particular embodiments, the ratio can be about 1:1 or 4:1. In another embodiment, the amount of the PDX:GOS combination may be between about 2.0 g/L and 8.0 g/L. In a particular embodiment, the amount of the PDX:GOS combination may be about 2 g/L of PDX and 2 g/L of GOS. At least 20% of the prebiotics can comprise galacto-oligosaccharide ("GOS"), polydextrose or a mixture thereof. The amount of each of GOS and/or polydextrose in the nutritional composition may, in an embodiment, be within the range of from about 1.0 g/L to about 4.0 g/L.

The nutritional composition of the disclosure may contain a source of long chain polyunsaturated fatty acid (LCPUFA) that comprises docosahexaenoic acid. Other suitable LCPUFAs include, but are not limited to, α-linoleic acid, γ-linoleic acid, linoleic acid, linolenic acid, docosahexaenoic acid (DHA), eicosapentaenoic acid (EPA) and arachidonic acid (ARA).

In an embodiment, especially if the nutritional composition is an infant formula, the nutritional composition is supplemented with both DHA and ARA. In this embodiment, the weight ratio of ARA:DHA may be between about 1:3 and about 9:1. In a particular embodiment, the ratio of ARA:DHA is from about 1:2 to about 4:1.

If included, the source of DHA and/or ARA may be any source known in the art such as marine oil, fish oil, single cell oil, egg yolk lipid, and brain lipid. In some embodiments, the DHA and ARA are sourced from single cell Martek oils, DHASCO® and ARASCO®, or variations thereof. The DHA and ARA can be in natural form, provided that the remainder of the LCPUFA source does not result in any substantial deleterious effect on the subject. Alternatively, the DHA and ARA can be used in refined form.

In an embodiment, sources of DHA and ARA are single cell oils as taught in U.S. Pat. Nos. 5,374,657; 5,550,156; and 5,397,591, the disclosures of which are incorporated herein in their entirety by reference. Nevertheless, the present disclosure is not limited to only such oils.

The nutritional composition may also comprise a source of 3-glucan. Glucans are polysaccharides, specifically polymers of glucose, which are naturally occurring and may be found in cell walls of bacteria, yeast, fungi, and plants. Beta glucans (β-glucans) are themselves a diverse subset of glucose polymers, which are made up of chains of glucose monomers linked together via beta-type glycosidic bonds to form complex carbohydrates.

β-1,3-glucans are carbohydrate polymers purified from, for example, yeast, mushroom, bacteria, algae, or cereals. (Stone B A, Clarke A E. Chemistry and Biology of (1-3)-Beta-Glucans. London:Portland Press Ltd; 1993.) The chemical structure of β-1,3-glucan depends on the source of the β-1,3-glucan. Moreover, various physiochemical parameters, such as solubility, primary structure, molecular weight, and branching, play a role in biological activities of β-1,3-glucans. (Yadomae T., Structure and biological activities of fungal beta-1,3-glucans. Yakugaku Zasshi. 2000; 120:413-431.)

β-1,3-glucans are naturally occurring polysaccharides, with or without β-1,6-glucose side chains that are found in the cell walls of a variety of plants, yeasts, fungi and bacteria. β-1,3; 1,6-glucans are those containing glucose units with (1,3) links having side chains attached at the (1,6) position(s). β-1,3; 1,6 glucans are a heterogeneous group of glucose polymers that share structural commonalities, including a backbone of straight chain glucose units linked by a β-1,3 bond with β-1,6-linked glucose branches extending from this backbone. While this is the basic structure for the presently described class of β-glucans, some variations may exist. For example, certain yeast β-glucans have additional regions of β(1,3) branching extending from the β(1,6) branches, which add further complexity to their respective structures.

β-glucans derived from baker's yeast, *Saccharomyces cerevisiae*, are made up of chains of D-glucose molecules connected at the 1 and 3 positions, having side chains of glucose attached at the 1 and 6 positions. Yeast-derived β-glucan is an insoluble, fiber-like, complex sugar having the general structure of a linear chain of glucose units with a β-1,3 backbone interspersed with β-1,6 side chains that are generally 6-8 glucose units in length. More specifically, β-glucan derived from baker's yeast is poly-(1,6)-β-D-glucopyranosyl-(1,3)-β-D-glucopyranose.

Furthermore, β-glucans are well tolerated and do not produce or cause excess gas, abdominal distension, bloating or diarrhea in pediatric subjects. Addition of β-glucan to a nutritional composition for a pediatric subject, such as an infant formula, a growing-up milk or another children's nutritional product, will improve the subject's immune response by increasing resistance against invading pathogens and therefore maintaining or improving overall health.

The nutritional composition of the present disclosure, may comprise lactoferrin. Lactoferrins are single chain polypeptides of about 80 kD containing 1-4 glycans, depending on the species. The 3-D structures of lactoferrin of different species are very similar, but not identical. Each lactoferrin comprises two homologous lobes, called the N- and C-lobes, referring to the N-terminal and C-terminal part of the molecule, respectively. Each lobe further consists of two sub-lobes or domains, which form a cleft where the ferric ion (Fe3+) is tightly bound in synergistic cooperation with a (bi)carbonate anion. These domains are called N1, N2, C1 and C2, respectively. The N-terminus of lactoferrin has strong cationic peptide regions that are responsible for a number of important binding characteristics. Lactoferrin has a very high isoelectric point (~pI 9) and its cationic nature plays a major role in its ability to defend against bacterial, viral, and fungal pathogens. There are several clusters of cationic amino acids residues within the N-terminal region of lactoferrin mediating the biological activities of lactoferrin against a wide range of microorganisms.

Lactoferrin for use in the present disclosure may be, for example, isolated from the milk of a non-human animal or produced by a genetically modified organism. The oral electrolyte solutions described herein can, in some embodiments comprise non-human lactoferrin, non-human lactoferrin produced by a genetically modified organism and/or human lactoferrin produced by a genetically modified organism.

Suitable non-human lactoferrins for use in the present disclosure include, but are not limited to, those having at least 48% homology with the amino acid sequence of human lactoferrin. For instance, bovine lactoferrin ("bLF") has an amino acid composition which has about 70% sequence homology to that of human lactoferrin. In some embodiments, the non-human lactoferrin has at least 65% homology with human lactoferrin and in some embodiments, at least 75% homology. Non-human lactoferrins acceptable for use in the present disclosure include, without limitation, bLF, porcine lactoferrin, equine lactoferrin, buffalo lactoferrin, goat lactoferrin, murine lactoferrin and camel lactoferrin.

In some embodiments, the nutritional composition of the present disclosure comprises non-human lactoferrin, for example bLF. bLF is a glycoprotein that belongs to the iron transporter or transferring family. It is isolated from bovine milk, wherein it is found as a component of whey. There are known differences between the amino acid sequence, glycosylation patters and iron-binding capacity in human lactoferrin and bLF. Additionally, there are multiple and sequential processing steps involved in the isolation of bLF from cow's milk that affect the physiochemical properties of the resulting bLF preparation. Human lactoferrin and bLF are also reported to have differences in their abilities to bind the lactoferrin receptor found in the human intestine.

Though not wishing to be bound by this or any other theory, it is believe that bLF that has been isolated from whole milk has less lipopolysaccharide (LPS) initially bound than does bLF that has been isolated from milk powder. Additionally, it is believed that bLF with a low somatic cell count has less initially-bound LPS. A bLF with less initially-bound LPS has more binding sites available on its surface. This is thought to aid bLF in binding to the appropriate location and disrupting the infection process.

bLF suitable for the present disclosure may be produced by any method known in the art. For example, in U.S. Pat. No. 4,791,193, incorporated by reference herein in its entirety, Okonogi et al. discloses a process for producing bovine lactoferrin in high purity. Generally, the process as disclosed includes three steps. Raw milk material is first contacted with a weakly acidic cationic exchanger to absorb lactoferrin followed by the second step where washing takes place to remove nonabsorbed substances. A desorbing step follows where lactoferrin is removed to produce purified bovine lactoferrin. Other methods may include steps as described in U.S. Pat. Nos. 7,368,141, 5,849,885, 5,919,913 and 5,861,491, the disclosures of which are all incorporated by reference in their entirety.

The lactoferrin that is used in certain embodiments may be any lactoferrin isolated from whole milk and/or having a low somatic cell count, wherein "low somatic cell count" refers to a somatic cell count less than 200,000 cells/mL. By way of example, suitable lactoferrin is available from Tatua Co-operative Dairy Co. Ltd., in Morrinsville, New Zealand, from FrieslandCampina Domo in Amersfoort, Netherlands or from Fonterra Co-Operative Group Limited in Auckland, New Zealand.

Surprisingly, lactoferrin included herein maintains certain bactericidal activity even if exposed to a low pH (i.e., below about 7, and even as low as about 4.6 or lower) and/or high temperatures (i.e., above about 65° C., and as high as about 120° C.), conditions which would be expected to destroy or severely limit the stability or activity of human lactoferrin. These low pH and/or high temperature conditions can be expected during certain processing regimen for nutritional compositions of the types described herein, such as pasteurization. Therefore, even after processing regimens, lactoferrin has bactericidal activity against undesirable bacterial pathogens found in the human gut. The nutritional composition may, in some embodiments, comprise lactoferrin in an amount from about 25 mg/100 mL to about 150 mg/100 mL. In other embodiments lactoferrin is present in an amount from about 60 mg/100 mL to about 120 mg/100 mL. In still other embodiments lactoferrin is present in an amount from about 85 mg/100 mL to about 110 mg/100 mL.

In an embodiment, the nutritional composition(s) of the present disclosure comprises choline. Choline is a nutrient that is essential for normal function of cells. It is a precursor for membrane phospholipids, and it accelerates the synthesis and release of acetylcholine, a neurotransmitter involved in memory storage. Moreover, though not wishing to be bound by this or any other theory, it is believed that dietary choline and docosahexaenoic acid (DHA) act synergistically to promote the biosynthesis of phosphatidylcholine and thus help promote synaptogenesis in human subjects. Additionally, choline and DHA may exhibit the synergistic effect of promoting dendritic spine formation, which is important in the maintenance of established synaptic connections. In some embodiments, the nutritional composition(s) of the present disclosure includes about 40 mg choline per serving to about 100 mg per 8 oz. serving.

In an embodiment, the nutritional composition comprises a source of iron. In an embodiment, the source of iron is ferric pyrophosphate, ferric orthophosphate, ferrous fumarate or a mixture thereof and the source of iron may be encapsulated in some embodiments.

One or more vitamins and/or minerals may also be added in to the nutritional composition in amounts sufficient to supply the daily nutritional requirements of a subject. It is to be understood by one of ordinary skill in the art that vitamin and mineral requirements will vary, for example, based on the age of the subject. For instance, an infant may have different vitamin and mineral requirements than a child between the ages of one and thirteen years. Thus, the embodiments are not intended to limit the nutritional composition to a particular age group but, rather, to provide a range of acceptable vitamin and mineral components.

In certain embodiments, the composition may optionally include, but is not limited to, one or more of the following vitamins or derivations thereof: vitamin B1 (thiamin, thiamin pyrophosphate, TPP, thiamin triphosphate, TTP, thiamin hydrochloride, thiamin mononitrate), vitamin B2 (riboflavin, flavin mononucleotide, FMN, flavin adenine dinucleotide, FAD, lactoflavin, ovoflavin), vitamin B3 (niacin, nicotinic acid, nicotinamide, niacinamide, nicotinamide adenine dinucleotide, NAD, nicotinic acid mononucleotide, NicMN, pyridine-3-carboxylic acid), vitamin B3-precursor tryptophan, vitamin B6 (pyridoxine, pyridoxal, pyridoxamine, pyridoxine hydrochloride), pantothenic acid (pantothenate, panthenol), folate (folic acid, folacin, pteroylglutamic acid), vitamin B12 (cobalamin, methylcobalamin, deoxyadenosylcobalamin, cyanocobalamin, hydroxycobalamin, adenosylcobalamin), biotin, vitamin C (ascorbic acid), vitamin A (retinol, retinyl acetate, retinyl palmitate, retinyl esters with other long-chain fatty acids, retinal, retinoic acid, retinol esters), vitamin D (calciferol, cholecalciferol, vitamin D3, 1,25,-dihydroxyvitamin D), vitamin E ($\alpha$-tocopherol, $\alpha$-tocopherol acetate, $\alpha$-tocopherol succinate, $\alpha$-tocopherol nicotinate, $\alpha$-tocopherol), vitamin K (vitamin K1, phylloquinone, naphthoquinone, vitamin K2, menaquinone-7, vitamin K3, menaquinone-4, menadione, menaquinone-8, menaquinone-8H, menaquinone-9, menaquinone-9H, menaquinone-10, menaquinone-11, menaquinone-12, menaquinone-13), choline, inositol, $\beta$-carotene and any combinations thereof.

In other embodiments, the composition may optionally include, but is not limited to, one or more of the following minerals or derivations thereof: boron, calcium, calcium acetate, calcium gluconate, calcium chloride, calcium lactate, calcium phosphate, calcium sulfate, chloride, chromium, chromium chloride, chromium picolonate, copper, copper sulfate, copper gluconate, cupric sulfate, fluoride, iron, carbonyl iron, ferric iron, ferrous fumarate, ferric orthophosphate, iron trituration, polysaccharide iron, iodide, iodine, magnesium, magnesium carbonate, magnesium hydroxide, magnesium oxide, magnesium stearate, magnesium sulfate, manganese, molybdenum, phosphorus, potassium, potassium phosphate, potassium iodide, potassium chloride, potassium acetate, selenium, sulfur, sodium, docusate sodium, sodium chloride, sodium selenate, sodium molybdate, zinc, zinc oxide, zinc sulfate and mixtures thereof. Non-limiting exemplary derivatives of mineral compounds include salts, alkaline salts, esters and chelates of any mineral compound.

The minerals can be added to growing-up milks or to other children's nutritional compositions in the form of salts such as calcium phosphate, calcium glycerol phosphate, sodium citrate, potassium chloride, potassium phosphate, magnesium phosphate, ferrous sulfate, zinc sulfate, cupric sulfate, manganese sulfate, and sodium selenite. Additional vitamins and minerals can be added as known within the art.

In an embodiment, the children's nutritional composition may contain between about 10 and about 50% of the maximum dietary recommendation for any given country, or between about 10 and about 50% of the average dietary recommendation for a group of countries, per serving of vitamins A, C, and E, zinc, iron, iodine, selenium, and choline. In another embodiment, the children's nutritional composition may supply about 10-30% of the maximum dietary recommendation for any given country, or about 10-30% of the average dietary recommendation for a group of countries, per serving of B-vitamins. In yet another embodiment, the levels of vitamin D, calcium, magnesium, phosphorus, and potassium in the children's nutritional product may correspond with the average levels found in milk. In other embodiments, other nutrients in the children's nutritional composition may be present at about 20% of the maximum dietary recommendation for any given country, or about 20% of the average dietary recommendation for a group of countries, per serving.

The children's nutritional composition of the present disclosure may optionally include one or more of the following flavoring agents, including, but not limited to, flavored extracts, volatile oils, cocoa or chocolate flavorings, peanut butter flavoring, cookie crumbs, vanilla or any commercially available flavoring. Examples of useful flavorings include, but are not limited to, pure anise extract, imitation banana extract, imitation cherry extract, chocolate extract, pure lemon extract, pure orange extract, pure peppermint extract, honey, imitation pineapple extract, imitation rum extract, imitation strawberry extract, or vanilla extract; or volatile oils, such as balm oil, bay oil, bergamot oil, cedarwood oil, cherry oil, cinnamon oil, clove oil, or peppermint oil; peanut butter, chocolate flavoring, vanilla cookie crumb, butterscotch, toffee, and mixtures thereof. The amounts of flavoring agent can vary greatly depending upon the flavoring agent used. The type and amount of flavoring agent can be selected as is known in the art.

The nutritional compositions of the present disclosure may optionally include one or more emulsifiers that may be added for stability of the final product. Examples of suitable emulsifiers include, but are not limited to, lecithin (e.g., from egg or soy), alpha lactalbumin and/or mono- and di-glycerides, and mixtures thereof. Other emulsifiers are readily apparent to the skilled artisan and selection of suitable emulsifier(s) will depend, in part, upon the formulation and final product.

The nutritional compositions of the present disclosure may optionally include one or more preservatives that may also be added to extend product shelf life. Suitable preservatives include, but are not limited to, potassium sorbate, sodium sorbate, potassium benzoate, sodium benzoate, calcium disodium EDTA, and mixtures thereof.

The nutritional compositions of the present disclosure may optionally include one or more stabilizers. Suitable stabilizers for use in practicing the nutritional composition of the present disclosure include, but are not limited to, gum arabic, gum ghatti, gum karaya, gum tragacanth, agar, furcellaran, guar gum, gellan gum, locust bean gum, pectin, low methoxyl pectin, gelatin, microcrystalline cellulose, CMC (sodium carboxymethylcellulose), methylcellulose hydroxypropyl methyl cellulose, hydroxypropyl cellulose, DATEM (diacetyl tartaric acid esters of mono- and diglycerides), dextran, carrageenans, and mixtures thereof.

The nutritional compositions of the disclosure may provide minimal, partial or total nutritional support. The compositions may be nutritional supplements or meal replacements. The compositions may, but need not, be nutritionally complete. In an embodiment, the nutritional composition of the disclosure is nutritionally complete and contains suitable types and amounts of lipid, carbohydrate, protein, vitamins and minerals. The amount of lipid or fat typically can vary from about 2 to about 7 g/100 kcal. The amount of protein typically can vary from about 1 to about 5 g/100 kcal. The amount of carbohydrate typically can vary from about 8 to about 14 g/100 kcal.

In some embodiments, the nutritional composition of the present disclosure is a growing-up milk. Growing-up milks are fortified milk-based beverages intended for children over 1 year of age (typically from 1-6 years of age). They are not medical foods and are not intended as a meal replacement or a supplement to address a particular nutritional deficiency. Instead, growing-up milks are designed with the intent to serve as a complement to a diverse diet to provide additional insurance that a child achieves continual, daily intake of all essential vitamins and minerals, macronutrients plus additional functional dietary components, such as non-essential nutrients that have purported health-promoting properties.

The exact composition of an infant formula or a growing-up milk or other nutritional composition according to the present disclosure can vary from market-to-market, depending on local regulations and dietary intake information of the population of interest. In some embodiments, nutritional compositions according to the disclosure consist of a milk protein source, such as whole or skim milk, plus added sugar and sweeteners to achieve desired sensory properties, and added vitamins and minerals. The fat composition is typically derived from the milk raw materials. Total protein can be targeted to match that of human milk, cow milk or a lower value. Total carbohydrate is usually targeted to provide as little added sugar, such as sucrose or fructose, as possible to achieve an acceptable taste. Typically, Vitamin A, calcium and Vitamin D are added at levels to match the nutrient contribution of regional cow milk. Otherwise, in some embodiments, vitamins and minerals can be added at levels that provide approximately 20% of the dietary reference intake (DRI) or 20% of the Daily Value (DV) per serving. Moreover, nutrient values can vary between markets depending on the identified nutritional needs of the intended population, raw material contributions and regional regulations.

The pediatric subject may be a child or an infant. For example, the subject may an infant ranging in age from 0 to 3 months, about 0 to 6 months, 0 to 12 months, 3 to 6 months, or 6 to 12 months. The subject may alternatively be a child ranging in age from 1 to 13 years, 1 to 6 years or 1 to 3 years. In an embodiment, the composition may be administered to the pediatric subject prenatally, during infancy, and during childhood.

Examples are provided to illustrate some embodiments of the nutritional composition of the present disclosure but should not be interpreted as any limitation thereon. Other embodiments within the scope of the claims herein will be apparent to one skilled in the art from the consideration of the specification or practice of the nutritional composition or methods disclosed herein. It is intended that the specification, together with the example, be considered to be exemplary only, with the scope and spirit of the disclosure being indicated by the claims which follow the example.

EXAMPLES

Example 1

The nutrient content of an example infant formula according to the present disclosure is provided in Table 3.

TABLE 3

Example composition nutrient content

| Nutrient | Amount Per 100 kcal | |
| --- | --- | --- |
| | Minimum | Maximum |
| Total protein (g) | 1.8 | 3.0 |
| Intact protein (g) | 1.35 | 2.85 |
| Milk peptides <10 kDa (g) | 0.09 | 0.75 |
| Fat (g) | 4.5 | 5.6 |
| Carbohydrates (g) | 10.0 | 14.0 |
| Prebiotic (g) | 0.1 | 1 |
| DHA (mg) | 5 | 30 |
| Beta glucan (mg) | 50 | 1000 |
| Probiotics (CFU) | $10^5$ | $10^9$ |
| Vitamin A (IU) | 200 | 800 |
| Vitamin D (IU) | 30 | 100 |
| Vitamin E (IU) | 1.5 | 5 |
| Vitamin K (mcg) | 8 | 30 |
| Thiamin (mcg) | 80 | 260 |
| Riboflavin (mcg) | 80 | 400 |
| Vitamin B6 (mcg) | 40 | 170 |
| Vitamin B12 (mcg) | 0.1 | 2 |
| Niacin (mcg) | 400 | 2400 |
| Folic Acid (mcg) | 8 | 40 |
| Pantothenic Acid (mcg) | 400 | 1500 |
| Biotin (mcg) | 2 | 10 |
| Vitamin C (mg) | 8 | 80 |
| Choline | 12 | 60 |
| Calcium (mg) | 50 | 150 |
| Phosphorus (mg) | 30 | 90 |
| Sodium (mg) | 15 | 50 |
| Potassium (mg) | 50 | 200 |
| Chloride (mg) | 30 | 100 |
| Iodine (mcg) | 5 | 40 |

TABLE 3-continued

Example composition nutrient content

| Nutrient | Amount Per 100 kcal | |
| --- | --- | --- |
| | Minimum | Maximum |
| Iron (mg) | 0.5 | 3.0 |
| Zinc (mg) | 0.1 | 2.0 |
| Manganese (mcg) | 10 | 100 |
| Copper (mcg) | 50 | 200 |
| Selenium (mcg) | 2 | 15 |

Example 2

An example composition according to ingredients is listed in Table 4.

TABLE A

Example ingredient composition

| Ingredient | Kg |
| --- | --- |
| Latose | 40.260 |
| Fat blend | 25.600 |
| Whey protein concentrate | 19.700 |
| Non-fat dry milk | 6.000 |
| Galactooligosaccharide | 3.680 |
| Milk protein hydrolysate | 3.100 |
| Polydextrose | 1.850 |
| Lecithin | 0.794 |
| Fungal-algal oil | 0.716 |
| Calcium carbonate | 0.450 |
| Choline chloride | 0.170 |
| Potassium citrate | 0.120 |
| Calcium phosphate tribasic | 0.110 |
| Potassium chloride | 0.018 |
| Magnesium oxide | 0.013 |
| L-carnitine | 0.011 |
| Sodium chloride | 0.006 |
| Vitamin premix | 0.321 |
| Mineral premix | 0.150 |
| Nucleotide premix | 0.166 |
| Iron trituration | 0.250 |

What is claimed is:

1. A nutritional composition comprising:
a protein source comprising an intact milk protein and a partially hydrolyzed milk protein comprising peptides having a molecular weight of less than 10 kDa, wherein the intact milk protein is present in an amount of from about 1.35 g per 100 kcal to about 2.85 g per 100 kcal and the peptides having a molecular weight of less than 10 kDa are present in an amount of from about 0.09 g per 100 kcal to about 0.75 g per 100 kcal, and further wherein the partially hydrolyzed milk protein includes each of the following individual peptides derived from β-lactoglobulin SEQ ID No. 3, SEQ ID No. 4, SEQ ID No. 5, and SEQ ID No. 8,
a fat source, and
a carbohydrate source,
wherein the intact milk protein comprises whey and casein having a whey to casein weight ratio ranging from about 80:20 to 50:50.

2. The composition of claim 1, wherein about 5% to about 25% of the total nitrogen content of the composition is provided by peptides in the partially hydrolyzed protein.

3. The composition of claim 1, wherein the hydrolyzed milk protein has a degree of hydrolysis ranging from about 4% to about 40%.

4. The composition of claim 1, wherein at least 75% by weight of the peptides have a molecular weight of less than 5 kDa.

5. The composition of claim 1, wherein the partially hydrolyzed milk protein comprises additional peptides derived from β-casein, α-S1-casein, κ-casein, α-lactalbumin, β-lactoglobulin, IL-2, TGF-β, IGF-1, GLYCAM-1, SPDR protein, and combinations thereof.

6. The nutritional composition of claim 1, wherein the partially hydrolyzed milk protein comprises at least five additional individual peptides selected from the group consisting of SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, SEQ ID No. 39, SEQ ID No. 40, SEQ ID No. 41, SEQ ID No. 42, SEQ ID No. 43, SEQ ID No. 44, SEQ ID No. 45, SEQ ID No. 46, SEQ ID No. 47, SEQ ID No. 48, SEQ ID No. 49, SEQ ID No. 50, SEQ ID No. 51, SEQ ID No. 52 and SEQ ID No 53.

7. The composition of claim 6, wherein the peptide has antioxidant activity, antimicrobial activity, immunomodulatory activity, acetyl choline transferase (ACE) inhibitory activity, or a combination thereof.

8. The composition of claim 1, wherein the peptides provide at least 5 mM Trolox equivalent antioxidant capacity to the composition.

9. The nutritional composition of claim 1, wherein the composition is an infant formula.

10. The composition of claim 1, further comprising a prebiotic.

11. The composition of claim 1, further comprising a source of docosahexaenoic acid.

12. The composition of claim 1, wherein the intact protein comprises about 75 to about 95% of the total nitrogen content of the composition.

13. The composition of claim 1, wherein less than 5% of the non-protein nitrogen in the composition comprises nucleotides, carnitine, lecithin or mixtures thereof.

14. The composition of claim 1, wherein about 5% to about 25% of total nitrogen content of the composition is non-protein nitrogen provided by the partially hydrolyzed milk protein.

15. The composition of claim 1, wherein the partially hydrolyzed protein further comprises at least one peptide selected from the group consisting of SEQ ID NO 1, SEQ ID NO 2, SEQ ID NO 6, SEQ ID NO 7, and SEQ ID NO 9.

16. The composition of claim 1, further comprising choline.

* * * * *

SEQUENCE LISTING

```
<160> NUMBER OF SEQ ID NOS: 53

<210> SEQ ID NO 1
<211> LENGTH: 5
<212> TYPE: PRT
<213> ORGANISM: bovinae

<400> SEQUENCE: 1

Val Pro Tyr Pro Gln
1               5

<210> SEQ ID NO 2
<211> LENGTH: 5
<212> TYPE: PRT
<213> ORGANISM: bovinae

<400> SEQUENCE: 2

Leu Pro Val Pro Gln
1               5

<210> SEQ ID NO 3
<211> LENGTH: 7
```

-continued

```
<212> TYPE: PRT
<213> ORGANISM: bovinae

<400> SEQUENCE: 3

Asp Asp Glu Ala Leu Glu Lys
1               5

<210> SEQ ID NO 4
<211> LENGTH: 6
<212> TYPE: PRT
<213> ORGANISM: bovinae

<400> SEQUENCE: 4

Val Glu Glu Leu Lys Pro
1               5

<210> SEQ ID NO 5
<211> LENGTH: 6
<212> TYPE: PRT
<213> ORGANISM: bovinae

<400> SEQUENCE: 5

Pro Glu Gly Asp Leu Glu
1               5

<210> SEQ ID NO 6
<211> LENGTH: 9
<212> TYPE: PRT
<213> ORGANISM: bovinae

<400> SEQUENCE: 6

Lys Glu Asp Val Pro Ser Glu Arg Tyr
1               5

<210> SEQ ID NO 7
<211> LENGTH: 8
<212> TYPE: PRT
<213> ORGANISM: bovinae

<400> SEQUENCE: 7

Asn Lys Pro Glu Asp Glu Thr His
1               5

<210> SEQ ID NO 8
<211> LENGTH: 7
<212> TYPE: PRT
<213> ORGANISM: bovinae

<400> SEQUENCE: 8

Ser Ala Pro Leu Arg Val Tyr
1               5

<210> SEQ ID NO 9
<211> LENGTH: 4
<212> TYPE: PRT
<213> ORGANISM: bovinae

<400> SEQUENCE: 9

Glu Val Pro Lys
1

<210> SEQ ID NO 10
<211> LENGTH: 9
<212> TYPE: PRT
<213> ORGANISM: bovinae
```

```
<400> SEQUENCE: 10

Val Pro Tyr Pro Gln Arg Asp Met Pro
1               5

<210> SEQ ID NO 11
<211> LENGTH: 8
<212> TYPE: PRT
<213> ORGANISM: bovinae

<400> SEQUENCE: 11

Lys Val Leu Pro Val Pro Gln Lys
1               5

<210> SEQ ID NO 12
<211> LENGTH: 9
<212> TYPE: PRT
<213> ORGANISM: bovinae

<400> SEQUENCE: 12

Ser Asp Ile Ser Leu Leu Asp Ala Gln
1               5

<210> SEQ ID NO 13
<211> LENGTH: 11
<212> TYPE: PRT
<213> ORGANISM: bovinae

<400> SEQUENCE: 13

Asp Asp Glu Ala Leu Glu Lys Phe Asp Lys Ala
1               5                   10

<210> SEQ ID NO 14
<211> LENGTH: 15
<212> TYPE: PRT
<213> ORGANISM: bovinae

<400> SEQUENCE: 14

Leu Lys Pro Thr Pro Glu Gly Asp Leu Glu Ile Leu Leu Gln Lys
1               5                   10                  15

<210> SEQ ID NO 15
<211> LENGTH: 15
<212> TYPE: PRT
<213> ORGANISM: bovinae

<400> SEQUENCE: 15

Leu Val Arg Thr Pro Glu Val Asp Asp Glu Ala Leu Glu Lys Phe
1               5                   10                  15

<210> SEQ ID NO 16
<211> LENGTH: 12
<212> TYPE: PRT
<213> ORGANISM: bovinae

<400> SEQUENCE: 16

Thr Pro Glu Val Asp Asp Glu Ala Leu Glu Lys Phe
1               5                   10

<210> SEQ ID NO 17
<211> LENGTH: 9
<212> TYPE: PRT
<213> ORGANISM: bovinae

<400> SEQUENCE: 17
```

```
Val Asp Asp Glu Ala Leu Glu Lys Phe
1               5

<210> SEQ ID NO 18
<211> LENGTH: 13
<212> TYPE: PRT
<213> ORGANISM: bovinae

<400> SEQUENCE: 18

Val Glu Glu Leu Lys Pro Thr Pro Glu Gly Asp Leu Glu
1               5                   10

<210> SEQ ID NO 19
<211> LENGTH: 18
<212> TYPE: PRT
<213> ORGANISM: bovinae

<400> SEQUENCE: 19

Val Glu Glu Leu Lys Pro Thr Pro Glu Gly Asp Leu Glu Ile Leu Leu
1               5                   10                  15

Gln Lys

<210> SEQ ID NO 20
<211> LENGTH: 6
<212> TYPE: PRT
<213> ORGANISM: bovinae

<400> SEQUENCE: 20

Val Glu Glu Leu Lys Pro
1               5

<210> SEQ ID NO 21
<211> LENGTH: 15
<212> TYPE: PRT
<213> ORGANISM: bovinae

<400> SEQUENCE: 21

Val Tyr Val Glu Glu Leu Lys Pro Thr Pro Glu Gly Asp Leu Glu
1               5                   10                  15

<210> SEQ ID NO 22
<211> LENGTH: 7
<212> TYPE: PRT
<213> ORGANISM: bovinae

<400> SEQUENCE: 22

Asp Asp Glu Ala Leu Glu Lys
1               5

<210> SEQ ID NO 23
<211> LENGTH: 15
<212> TYPE: PRT
<213> ORGANISM: bovinae

<400> SEQUENCE: 23

Leu Lys Pro Thr Pro Glu Gly Asp Leu Glu Ile Leu Leu Gln Lys
1               5                   10                  15

<210> SEQ ID NO 24
<211> LENGTH: 12
<212> TYPE: PRT
<213> ORGANISM: bovinae

<400> SEQUENCE: 24
```

```
Arg Thr Pro Glu Val Asp Asp Glu Ala Leu Glu Lys
1               5                   10
```

<210> SEQ ID NO 25
<211> LENGTH: 9
<212> TYPE: PRT
<213> ORGANISM: bovinae

<400> SEQUENCE: 25

```
Ile Gly Ser Glu Asn Ser Glu Lys Thr
1               5
```

<210> SEQ ID NO 26
<211> LENGTH: 12
<212> TYPE: PRT
<213> ORGANISM: bovinae

<400> SEQUENCE: 26

```
His Ile Gln Lys Glu Asp Val Pro Ser Glu Arg Tyr
1               5                   10
```

<210> SEQ ID NO 27
<211> LENGTH: 9
<212> TYPE: PRT
<213> ORGANISM: bovinae

<400> SEQUENCE: 27

```
Lys Glu Asp Val Pro Ser Glu Arg Tyr
1               5
```

<210> SEQ ID NO 28
<211> LENGTH: 9
<212> TYPE: PRT
<213> ORGANISM: bovinae

<400> SEQUENCE: 28

```
Leu Asn Lys Pro Glu Asp Glu Thr His
1               5
```

<210> SEQ ID NO 29
<211> LENGTH: 14
<212> TYPE: PRT
<213> ORGANISM: bovinae

<400> SEQUENCE: 29

```
Asn Lys Pro Glu Asp Glu Thr His Leu Glu Ala Gln Pro Thr
1               5                   10
```

<210> SEQ ID NO 30
<211> LENGTH: 10
<212> TYPE: PRT
<213> ORGANISM: bovinae

<400> SEQUENCE: 30

```
Val Ile Glu Ser Pro Pro Glu Ile Asn Thr
1               5                   10
```

<210> SEQ ID NO 31
<211> LENGTH: 20
<212> TYPE: PRT
<213> ORGANISM: bovinae

<400> SEQUENCE: 31

```
Trp Leu Val Ile Ser Val Leu Ala Ile Ser Leu Ala Ser Ser Val Thr
```

Glu Asp Val Cys
        20

<210> SEQ ID NO 32
<211> LENGTH: 13
<212> TYPE: PRT
<213> ORGANISM: bovinae

<400> SEQUENCE: 32

Asn Glu Leu Thr Asn Ser Thr Leu Ala Thr Asp Pro Pro
1               5                   10

<210> SEQ ID NO 33
<211> LENGTH: 19
<212> TYPE: PRT
<213> ORGANISM: bovinae

<400> SEQUENCE: 33

Gln Asn Ala Val Pro Tyr Pro Gly Gly Gln Gly Glu Ala Glu Arg Phe
1               5                   10                  15

Met Thr Pro

<210> SEQ ID NO 34
<211> LENGTH: 23
<212> TYPE: PRT
<213> ORGANISM: bovinae

<400> SEQUENCE: 34

Ile Thr Leu His Glu Ala Leu Ala Ala Ala Asp Asp Leu Ser Lys Gln
1               5                   10                  15

Gly Ile Ser Leu Arg Val Ile
        20

<210> SEQ ID NO 35
<211> LENGTH: 17
<212> TYPE: PRT
<213> ORGANISM: bovinae

<400> SEQUENCE: 35

Ala Ser Asp Ile Ser Leu Leu Asp Ala Gln Ser Ala Pro Leu Arg Val
1               5                   10                  15

Tyr

<210> SEQ ID NO 36
<211> LENGTH: 7
<212> TYPE: PRT
<213> ORGANISM: bovinae

<400> SEQUENCE: 36

Ser Ala Pro Leu Arg Val Tyr
1               5

<210> SEQ ID NO 37
<211> LENGTH: 10
<212> TYPE: PRT
<213> ORGANISM: bovinae

<400> SEQUENCE: 37

Phe Asp Lys Ala Leu Lys Ala Leu Pro Met
1               5                   10

```
<210> SEQ ID NO 38
<211> LENGTH: 10
<212> TYPE: PRT
<213> ORGANISM: bovinae

<400> SEQUENCE: 38

Ile Ile Ala Glu Lys Thr Lys Ile Pro Ala
1               5                   10

<210> SEQ ID NO 39
<211> LENGTH: 12
<212> TYPE: PRT
<213> ORGANISM: bovine

<400> SEQUENCE: 39

Lys Val Leu Val Leu Asp Thr Asp Tyr Lys Lys Tyr
1               5                   10

<210> SEQ ID NO 40
<211> LENGTH: 10
<212> TYPE: PRT
<213> ORGANISM: bovinae

<400> SEQUENCE: 40

Leu Ile Val Thr Gln Thr Met Lys Gly Leu
1               5                   10

<210> SEQ ID NO 41
<211> LENGTH: 3
<212> TYPE: PRT
<213> ORGANISM: bovinae

<400> SEQUENCE: 41

Leu Lys Pro
1

<210> SEQ ID NO 42
<211> LENGTH: 10
<212> TYPE: PRT
<213> ORGANISM: bovinae

<400> SEQUENCE: 42

His Lys Glu Met Pro Phe Pro Lys Tyr Pro
1               5                   10

<210> SEQ ID NO 43
<211> LENGTH: 10
<212> TYPE: PRT
<213> ORGANISM: bovinae

<400> SEQUENCE: 43

His Gln Pro His Gln Pro Leu Pro Pro Thr
1               5                   10

<210> SEQ ID NO 44
<211> LENGTH: 11
<212> TYPE: PRT
<213> ORGANISM: bovinae

<400> SEQUENCE: 44

Ser Gln Ser Lys Val Leu Pro Val Pro Gln Lys
1               5                   10

<210> SEQ ID NO 45
<211> LENGTH: 13
```

```
<212> TYPE: PRT
<213> ORGANISM: bovinae

<400> SEQUENCE: 45

Ser Ser Arg Gln Pro Gln Ser Gln Asn Pro Lys Leu Pro
1               5                   10

<210> SEQ ID NO 46
<211> LENGTH: 8
<212> TYPE: PRT
<213> ORGANISM: bovinae

<400> SEQUENCE: 46

Leu Ser Arg Tyr Pro Ser Tyr Gly
1               5

<210> SEQ ID NO 47
<211> LENGTH: 10
<212> TYPE: PRT
<213> ORGANISM: bovinae

<400> SEQUENCE: 47

Lys Ile Leu Asp Lys Val Gly Ile Asn Tyr
1               5                   10

<210> SEQ ID NO 48
<211> LENGTH: 9
<212> TYPE: PRT
<213> ORGANISM: bovinae

<400> SEQUENCE: 48

Val Val Gly Arg Gly Pro Gly Thr Pro
1               5

<210> SEQ ID NO 49
<211> LENGTH: 31
<212> TYPE: PRT
<213> ORGANISM: bovinae

<400> SEQUENCE: 49

Tyr Lys Glu Thr Leu Lys Ile Gln Asn Leu Glu Leu Lys Leu Ser Gly
1               5                   10                  15

Asp Ser Arg Ala Ser Arg Thr Lys Ser Thr Pro Ser Thr Cys Glu
            20                  25                  30

<210> SEQ ID NO 50
<211> LENGTH: 19
<212> TYPE: PRT
<213> ORGANISM: bovinae

<400> SEQUENCE: 50

Leu Ala Ser Ile Met Asn Pro Lys Ser Leu Thr Ile Gly Pro Arg Asp
1               5                   10                  15

Lys Pro Thr

<210> SEQ ID NO 51
<211> LENGTH: 13
<212> TYPE: PRT
<213> ORGANISM: bovinae

<400> SEQUENCE: 51

Tyr Lys Glu Thr Leu Asn Leu Lys Ser Gln Val Gln Lys
1               5                   10
```

```
<210> SEQ ID NO 52
<211> LENGTH: 25
<212> TYPE: PRT
<213> ORGANISM: bovinae

<400> SEQUENCE: 52

Leu Lys Pro Glu Gly Glu Ala Arg His Pro Leu Thr Thr Ser Pro Ser
1               5                   10                  15

His Arg Gly Gln Arg Lys Val Pro Ile
            20                  25

<210> SEQ ID NO 53
<211> LENGTH: 13
<212> TYPE: PRT
<213> ORGANISM: bovinae

<400> SEQUENCE: 53

Glu Val Pro Lys Pro Glu Val Ile Phe Lys Leu Glu Gln
1               5                   10
```